United States Patent
Sournac et al.

(10) Patent No.: US 9,320,612 B2
(45) Date of Patent: Apr. 26, 2016

(54) CORPORECTOMY IMPLANT

(75) Inventors: Denys Sournac, Reyrieux (FR); David Ryan, Collonges-au-Mont-d'Or (FR)

(73) Assignee: MEDICREA INTERNATIONAL, Neyron (FR)

( * ) Notice: Subject to any disclaimer, the term of this patent is extended or adjusted under 35 U.S.C. 154(b) by 257 days.

(21) Appl. No.: 13/982,794

(22) PCT Filed: Feb. 1, 2012

(86) PCT No.: PCT/IB2012/050466
§ 371 (c)(1),
(2), (4) Date: Jul. 31, 2013

(87) PCT Pub. No.: WO2012/104796
PCT Pub. Date: Aug. 9, 2012

(65) Prior Publication Data
US 2013/0310938 A1  Nov. 21, 2013

(30) Foreign Application Priority Data

Feb. 3, 2011 (FR) ..................... 11 50887

(51) Int. Cl.
*A61F 2/44* (2006.01)
*A61F 2/30* (2006.01)
*A61F 2/46* (2006.01)

(52) U.S. Cl.
CPC .............. *A61F 2/4425* (2013.01); *A61F 2/44* (2013.01); *A61F 2/4455* (2013.01); *A61F 2/4465* (2013.01); *A61F 2002/305* (2013.01); *A61F 2002/30028* (2013.01); *A61F 2002/3055* (2013.01); *A61F 2002/30121* (2013.01); *A61F 2002/30187* (2013.01); *A61F 2002/30235* (2013.01); *A61F 2002/30393* (2013.01); *A61F 2002/30395* (2013.01); *A61F 2002/30405* (2013.01);

(Continued)

(58) Field of Classification Search
CPC ............ A61F 2002/30601; A61F 2002/30028; A61F 2002/30121; A61F 2002/30187; A61F 2002/30235; A61F 2002/30393; A61F 2002/30395; A61F 2002/30495; A61F 2002/30504; A61F 2002/20512; A61F 2002/3055; A61F 2002/30807; A61F 2002/30817; A61F 2002/30838; A61F 2002/30911; A61F 2002/4627
See application file for complete search history.

(56) References Cited

U.S. PATENT DOCUMENTS

| | | | |
|---|---|---|---|
| 6,302,914 B1 | 10/2001 | Michelson | |
| 2008/0114467 A1* | 5/2008 | Capote et al. | 623/23.47 |
| 2009/0164017 A1 | 6/2009 | Sommerich | |

FOREIGN PATENT DOCUMENTS

| | | |
|---|---|---|
| EP | 0 968 692 | 1/2000 |
| WO | 03/013396 | 2/2003 |
| WO | 2009120618 | 10/2009 |

OTHER PUBLICATIONS

International Search Report dated May 11, 2012, corresponding to PCT/IB2012/050466.

*Primary Examiner* — Samuel Hanna
(74) *Attorney, Agent, or Firm* — Young & Thompson

(57) ABSTRACT

This Implant (1) includes, in a known manner, two pieces (2, 3) that are telescopically mobile relative to one another and elements (4) for positioning one piece (3) in a particular position relative to the other piece (2), the two pieces (2, 3) being made from a polymer material. At least one of the two pieces (2, 3) has a plurality of micro-cavities (15, 20, 32) over at least one wide portion of its peripheral wall (5); and the implant includes internal communications (16, 21, 33) in its wall(s) (5, 7, 31) including the micro-cavities (15, 20, 32), connecting all or some of the micro-cavities to one another.

12 Claims, 3 Drawing Sheets

(52) U.S. Cl.
CPC ............... *A61F2002/30495* (2013.01); *A61F 2002/30504* (2013.01); *A61F 2002/30512* (2013.01); *A61F 2002/30556* (2013.01); *A61F 2002/30578* (2013.01); *A61F 2002/30579* (2013.01); *A61F 2002/30594* (2013.01); *A61F 2002/30601* (2013.01); *A61F 2002/30807* (2013.01); *A61F 2002/30817* (2013.01); *A61F 2002/30838* (2013.01); *A61F 2002/30911* (2013.01); *A61F 2002/4627* (2013.01)

CORPORECTOMY IMPLANT

The present invention relates to a corporectomy implant, i.e. an implant intended to form a spacer between the vertebral bodies of two vertebrae situated on either side of an equipped vertebra, the body of that equipped vertebra having been subject to a partial ablation and receiving said implant.

Certain afflictions of a vertebra may require a total or partial ablation of the vertebral body, which involves the placement of a so-called "corporectomy" implant between the lower plate of the superjacent vertebra and the upper plate of the underlying vertebra. This implant thus makes it possible to functionally replace the vertebral body removed or hollowed out with a housing for receiving the implant, so as to reestablish the continuity of the vertebral column.

The placement of such a corporectomy implant involves immobilizing the superjacent vertebra and the underlying vertebra relative to the equipped vertebra.

According to an existing technique, the corporectomy implant is in the form of a tube with a fine openwork wall; this type of implant is known as a "mesh." Such an implant is designed to inwardly contain one or more bone grafts and to be incorporated into the remaining portion of the equipped vertebral body, through growth of the bone cells through its openwork wall.

This implant has the advantage of allowing good osteo-integration of the implant into said remaining portion of the vertebral body; it has the drawback, however, of having a fine structure, and therefore risking becoming inserted into the plates of the superjacent and underlying vertebrae. Furthermore, not being adjustable lengthwise, it is necessary to select the implant of the correct height from among a range of implants of different heights; however, it is difficult to determine this dimension, given that the vertebrae are not, at the time of implantation, in an anatomical position. This type of implant also involves placing an anterior and/or posterior stabilization system of the vertebral column, such as an anterior plate fastened by screws and/or a posterior system with pedicle screws and connecting bars.

According to another existing technique, a corporectomy implant has a rigid metallic structure, with thick walls, and is formed from two assembled parts, telescopically mobile relative to one another. The implant is placed relatively easy to place, its two telescoping parts being in a folded state, and is then deployed to the appropriate height, by maneuvering means for actuating said telescoping parts. Such an implant does, however, have the drawback of not being able to ensure very good osteo-integration, and consequently always making the placement of an anterior and/or posterior stabilization system necessary. In fact, an implant of this type has an outwardly smooth wall, not intended to be maintained relative to the vertebral body by bone cell growth. In that case, the implant is maintained solely by friction with the vertebral plates of the superjacent and underlying vertebrae and by the stabilization system. Another existing implant of this type has large outer recesses in its wall, which are also not favorable to good osteo-integration of the implant.

Other drawbacks of this metal implant with a thick wall are its substantial rigidity, which does not correspond to the slight flexibility of the bones of the vertebrae, and the need to have a wide approach involving a complex surgical maneuver.

The publication of patent no. US 2008/114467 A1 discloses a corporectomy implant comprising two pieces that are telescopically mobile relative to one another and means for positioning one piece in a particular position relative to the other piece, the two pieces being made from a polymer material, and at least one of the two pieces having a plurality of cavities on at least one wide portion of its peripheral wall.

This implant is not fully satisfactory in practice.

The present invention aims to resolve all of the aforementioned drawbacks.

The aim of the invention is therefore to provide a corporectomy implant whereof the osteo-integration can be done under the best possible conditions, to the point of greatly reducing, or even eliminating, the need for an anterior and/or posterior stabilization system, and involving as reduced an approach as possible.

The concerned implant comprises, in a known manner, two pieces that are telescopically mobile relative to one another and means for positioning one piece in a determined position among a plurality of positions relative to the other piece, the two pieces being made from a polymer material.

According to the invention,
- at least one of the two pieces has a plurality of micro-cavities over at least one wide portion of its peripheral wall;
- the implant comprises internal communications in its wall(s) comprising the micro-cavities, connecting all or some of the micro-cavities to one another.

The invention thus consists of taking the opposite course to the existing technique, by going against the prejudice according to which a corporectomy implant with a telescoping structure must be made from a metal and rigid material, and must be kept in position by an anterior and/or posterior stabilization system. The invention consists of providing an implant (i) made from a polymer material, substantially less rigid than a metal material, (ii) whereof the wall has many micro-cavities intended to be invaded by bone cells during growth, and (iii) internal communications connecting all or some of the micro-cavities to one another, allowing a wide diffusion of the growing bone cells in the wall(s) of the implant, and are therefore very favorable to complete osteo-integration of the implant.

As a result, the implant according to the invention is better adapted to the features of the bones of the vertebrae than the existing implants, and can be completely osteo-integrated into the remaining portion of an equipped vertebral body, which can make it unnecessary to place anterior and/or posterior stabilization systems, all while preserving the advantages of a telescopic structure. This implant then involves a more reduced approach than in the existing technique, and involves a simpler surgical maneuver. In particular, the placement of this implant only requires a channel in the vertebral body to be equipped, and not a complete ablation of that body.

"Micro-cavities" refer to cavities, holes, or channels, having a transverse section smaller than 1 mm$^2$, in particular in the vicinity of 0.25 mm$^2$.

All or some of said internal communications can be longitudinal, i.e. parallel to the direction of telescopic sliding of the two telescoping pieces of the implant, therefore putting the micro-cavities situated in an upper position in the longitudinal direction in communication with the micro-cavities situated in a lower position.

Alternatively or cumulatively, all or some of these internal communications can be circumferential, i.e. connecting consecutive micro-cavities in a plane perpendicular or substantially perpendicular to the direction of telescopic sliding.

An implant including such internal indications can in particular be made using a so-called "additive" manufacturing method, known in itself, consisting of making the implant layer by layer, by superimposing layers along the telescopic sliding axis of said pieces, made up of a thermofusible powder; the fusion of the particles is done at determined locations, i.e. outside zones that must correspond to the aforementioned micro-cavities and any internal communications, and the non-fused particles are eliminated after the formation of one or more of said layers.

Preferably, the implant also comprises micro-cavities in at least at one of its longitudinal end walls, i.e. at least one of its walls intended to bear against the vertebral plates of the superjacent and underlying vertebrae when the implant is placed.

These micro-cavities also allow osteo-integration of the implant at these vertebral plates.

In the same manner as before, the implant can comprise internal communications formed in this or these longitudinal end wall(s), connecting all or some of the micro-cavities to one another. In particular, the micro-cavities can be formed in concentric circles, and the internal communications can extend along the radii of said circles, thereby putting the micro-cavities aligned in those radii in communication.

The invention will be well understood, and other features and advantages thereof will appear, in reference to the appended diagrammatic drawing, showing, as a non-limiting example, one embodiment of the corporectomy implant to which it relates.

Figure 8:
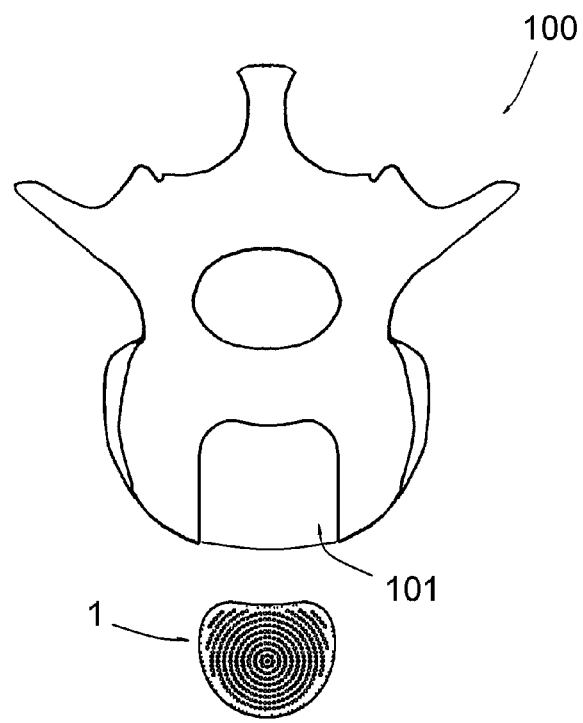
FIG. 8 is a view, in a cervico-caudal direction, of a vertebra to be equipped, before placement of the implant.

FIGS. 1 to 7 illustrate a corporectomy implant 1, i.e. an implant intended to form a spacer between the vertebral bodies of two vertebrae situated on either side of an equipped vertebra. FIG. 8 shows said vertebra 100 to be equipped, before placement of the implant 1.

As appears in FIGS. 1 to 7, the implant 1 is made up of three pieces, i.e. two telescoping pieces 2, 3 and the member 4 for actuating said pieces.

These three pieces 2, 3, 4 are made from a thermofusible polymer material, in particular PEKK (polyether ketone ketone).

The piece 2 is the base part of the implant 1, intended to rest against the plate of the underlying vertebra. It assumes the form of a body elongated in the direction of the height of the implant 1, having a peripheral wall 5, an upper longitudinal end wall 6, and a lower longitudinal end wall 7.

It will be understood that the terms "upper" and "lower," like the terms "anterior," "lateral" and "posterior," used below must be considered relative to the position of the implant 1 once it is placed on the vertebra 100.

The piece 2 has, in transverse section, a shape substantially copying that of a vertebral plate, i.e. a "D," with rounded anterior and lateral surfaces and a concave posterior surface. It has an increased thickness at its portions extending between its lateral surfaces and its posterior surface.

Figure 1:
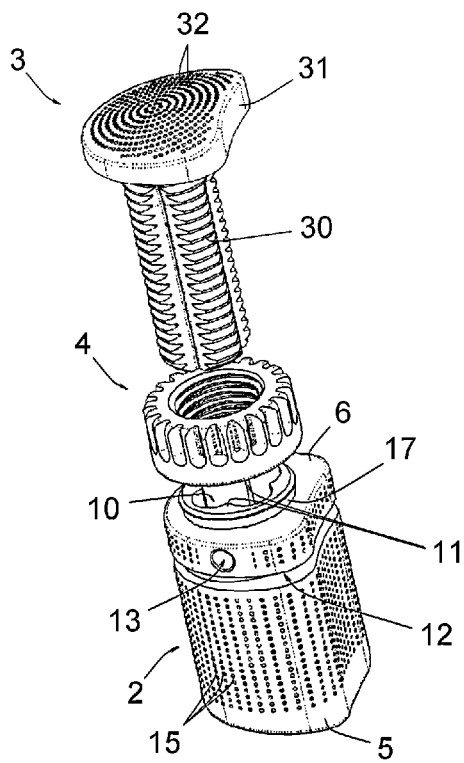
FIG. 1 is an exploded perspective view of two telescoping pieces and the member for actuating those pieces that it comprises, separated from one another.
Figure 2:
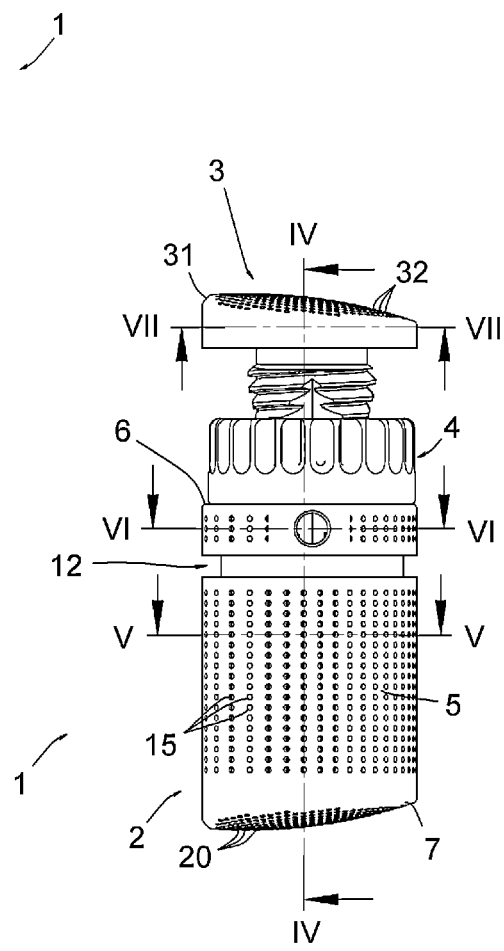
FIG. 2 is a side view, said telescoping pieces and said actuating member being in the assembly position.
Figure 3:
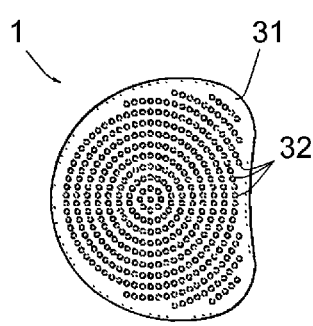
FIG. 3 is a top view.
Figure 4:
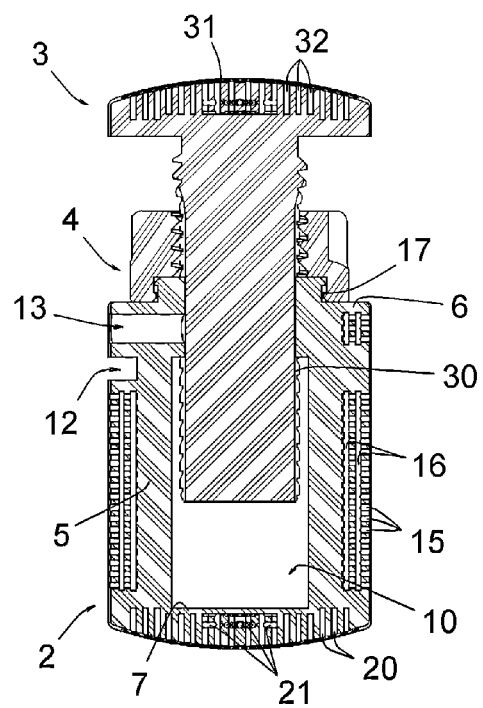
FIG. 4 is a cross-sectional view along line IV-IV of FIG. 2.
Figure 5:
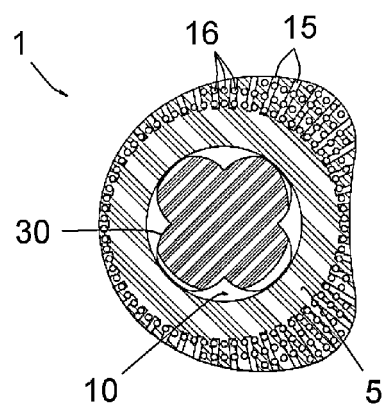
FIG. 5 is a cross-sectional view along line V-V of FIG. 2.
Figure 6:
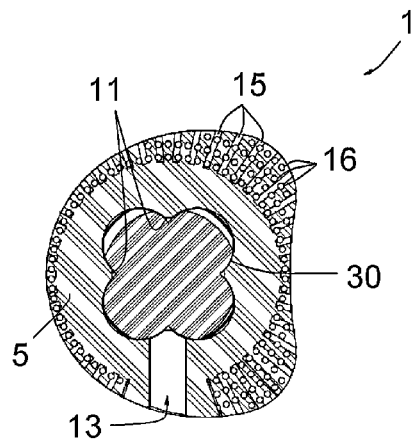
FIG. 6 is a cross-sectional view along line VI-VI of FIG. 2.
Figure 7:
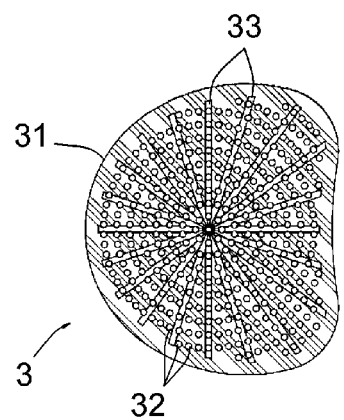
FIG. 7 is a cross-sectional view along line VII-VII of FIG. 2.

The piece 2 delimits an inner cavity 10 emerging in said upper wall 6, which has a circular transverse section inside the piece 2, as visible in FIGS. 4 and 5, and a quadrilobed transverse section at the upper wall 6, as visible in FIGS. 1 and 6.

The upper wall 6 in fact forms four equidistant longitudinal ribs 11 at its surface defining said cavity 10.

Said piece 2 has a peripheral slot 12 at its upper portion, allowing it to be grasped using a handling instrument, as well as a lateral hole 13 at said upper wall 6, emerging in the cavity 10, intended to receive a corresponding lug of said handling instrument, in order to secure the grasping of the implant.

As shown in the figures, the peripheral wall 5 has, outside the slot 12 and the hole 13, over practically the entire height thereof, a plurality of micro-cavities 15 connected to one another by series of longitudinal internal communications 16.

Each micro-cavity is formed by a more or less elongated hole, having a transverse section smaller than 1 $mm^2$, in particular in the vicinity of 0.25 $mm^2$.

In the illustrated example, the micro-cavities 15 are arranged in the form of a series positioned longitudinally, regularly distributed over the entire periphery of the piece 2. It appears in FIGS. 4 to 6 that they are formed substantially radially, over only part of the thickness of the peripheral wall 5, therefore without emerging in the cavity 10. Their bottoms are positioned substantially in a circle concentric to the axis of said cavity 10, from which it results that these micro-cavities 15 have much greater lengths at the thick latero-posterior portions of the peripheral wall 5 than at the anterior surface of that same wall 5 (cf. FIGS. 5 and 6).

The longitudinal internal communications 16 are distributed in several concentric series; the radially innermost series is formed on the entire periphery of the wall 5, except at the opening of the hole 13; second, third and fourth series extend at the thick latero-posterior portions of the wall 5 (cf. FIGS. 5 and 6).

The upper wall 6 forms a boss 17 coaxial to the cavity 10, whereof the upper portion has a rounded annular protrusion capable of allowing snapping of the actuating member 4 on the piece 2.

The inner wall 7 has an inclined (cf. FIG. 2) and curved (cf. FIG. 4) shape, adapted to bearing on the vertebral plate of the underlying vertebra. It also comprises a plurality of micro-cavities 20, formed parallel to one another, in the longitudinal direction of the piece 2 (cf. FIG. 4), and positioned in concentric circles or circle portions, like the micro-cavities 32 comprised by the piece 3, described below, appearing in FIG. 3. These micro-cavities 20 are connected to one another by internal communications 21 extending radially, like the internal communications 33 comprised by the piece 3, visible in FIG. 7.

The piece 3 has a threaded body 30 and a head 31.

The threaded body 30 has a quadrilobed transverse section adapted to be engaged on the ribs 11 so as to be wedged in rotation, but while still being able to slide along said ribs 11 (cf. FIG. 4). Its thread is adapted to cooperate with a tapping comprised by the actuating member 4.

The head 31 has, in transverse section, a shape similar to that of the piece 2 and that of the lower wall 7, and is thus adapted to bear against the vertebral plate of the superjacent vertebra. It has micro-cavities 32, arranged parallel to one another, in the longitudinal direction of the piece 2 (cf. FIG. 4), positioned in concentric circles or circle portions (cf. FIG. 3). These micro-cavities 32 are connected to one another by internal communications 33 extending radially (cf. FIG. 7).

The actuating member 4 assumes the form of a toothed wheel. It comprises a lower cavity allowing it to be engaged on the boss 17 and to be axially retained on the piece 2 by clipping on the rounded annular protrusion comprised by said boss 17. Over the rest of its height, it forms a tapped hole whereof the tapping is capable of engaging with the thread of the threaded body 31 of the piece 3.

The implant 1, including the aforementioned internal communications 16, 21, 33, is made using the so-called "additive" manufacturing method, known in itself, consisting of making the pieces 2 and 3 layer by layer, along the telescoping sliding axis of said pieces 2 and 3; more specifically:

a) a layer of thermofusible powder is placed in the bottom of a suitable mold;

b) fusion of the particles of that layer is done in zones that must correspond to the micro-cavities 15, 20, 32 and the internal communications 16, 21, 33;

c) the non-fused particles are eliminated;

d) a subsequent layer of thermofusible material is placed on the layer previously formed and the operations of steps b) and c) above are repeated; and e) the operations of step d) are repeated as many times as necessary to form the pieces 2 and 3.

Figure 9:
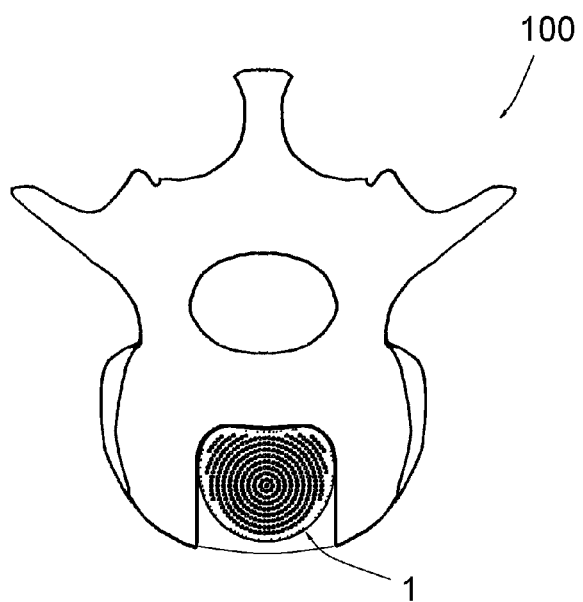
FIG. 9 is a view of that vertebra similar to FIG. 8, after placement of the implant.

To place the implant 1, a housing 101 is formed in the body of the vertebra 100 to be equipped, at the anterior surface thereof and over the entire height thereof, said housing 101 having dimensions adjusted to that of the implant 1 (cf. FIG. 8). The latter is then inserted into the housing 101 (cf. FIG. 9), while the piece 3 is retracted into the piece 2. The actuating member 4 is then rotated so as to deploy the piece 3 relative to the piece 2 to a sufficient position to ensure complete bearing of the implant 1 against the plates of the superjacent and underlying vertebrae. The lateral hole 13, which is threaded, can then receive a screw bearing against the threaded body 30 so as to completely immobilize the piece 2 relative to the piece 3.

As appears from the preceding, the invention provides a corporectomy implant having the decisive advantages of being able to be osteo-integrated under the best possible conditions into the equipped vertebra, to the point of greatly reducing, or even eliminating, the need for an anterior and/or posterior stabilization system, and involving only a reduced approach.

The invention was described above in reference to one embodiment provided as an example. It goes without saying that it is not limited to that embodiment, but rather that it extends to all embodiments covered by the appended claims.

The invention claimed is:

1. A corporectomy implant comprising:
    two pieces made of a polymer material that are telescopically mobile relative to one another along a longitudinal axis, a first piece of the two pieces being a base part that has a lower longitudinal end wall and a peripheral side wall defining an internal cavity in the base part, the peripheral side wall extending along the longitudinal axis from the lower longitudinal end wall to an upper longitudinal end wall, a second piece of the two pieces having a head and a longitudinal body depending from the head along the longitudinal axis and configured to be received in the internal cavity of the base part;
    an actuator that locks one of said two pieces in a determined axial position, along the longitudinal axis, among a plurality of axial positions along the longitudinal axis relative to the other of said two pieces;
    a plurality of micro-cavities over at least one wide portion of the peripheral side wall of the base part, the micro-cavities being cavities, holes or channels that extend only part-way through a thickness of the peripheral side wall and that have a transverse section relative to a longitudinal direction of telescopic sliding of the two pieces, along the longitudinal axis, with an area smaller than 1 mm$^2$; and
    a plurality of internal channels in the peripheral side wall passing through and connecting all or some of the plurality of the micro-cavities to one another.

2. The implant according to claim 1, wherein at least one of said upper and lower longitudinal end walls and said head comprises further ones of the micro-cavities.

3. The implant according to claim 1, wherein all or some of said plurality of the internal channels are parallel to the longitudinal direction, and wherein the plurality of the micro-cavities of the peripheral side wall in an upper position in the longitudinal direction are in communication with the plurality of the micro-cavities situated in a lower position in the longitudinal direction via the plurality of internal channels.

4. The implant according to claim 2, further comprising additional internal channels that connect consecutive ones of said further micro-cavities and that extend transverse to the longitudinal direction of telescopic sliding.

5. The implant according to claim 1, wherein the area of said transverse section of said micro-cavities is 0.25 mm$^2$.

6. The implant according to claim 4, wherein said further micro-cavities are in concentric circles, and said additional internal channels extend along radii of said circles, and wherein the further micro-cavities aligned in said radii are in communication with each other.

7. The implant according to claim 1, wherein said base part has, in a transverse section, rounded anterior and lateral surfaces and a concave posterior surface, and the peripheral side wall of the base part has an increased thickness at portions extending between the lateral surfaces and the posterior surface.

8. The implant according to claim 7, wherein the micro-cavities in said base part are arranged radially with respect to the longitudinal axis, wherein the micro-cavities located at the portions with increased thickness of the peripheral side wall have greater lengths than the micro-cavities located at the anterior surface of the peripheral side wall.

9. The implant according to claim 7, wherein the internal channels of said base part are distributed in plural concentric series and extend in the longitudinal direction, a first of said series being a radially innermost series formed on an entire periphery of the peripheral side wall, and second, third and fourth of said series extending at the increased thickness latero-posterior portions of the peripheral side wall.

10. The implant according to claim 7, wherein the second piece of said two pieces has, in a transverse section, rounded anterior and lateral surfaces and a concave posterior surface.

11. The implant according to claim 10, wherein said head comprises further micro-cavities that are parallel to one another.

12. A method for placing the implant according to claim 1 between adjacent vertebral bodies, comprising:
    forming a housing in the adjacent vertebral bodies to be equipped with the implant at an anterior surface thereof and over an entire height thereof, said housing having dimensions adjusted to that of the implant;
    inserting the implant into the housing, while the two pieces are telescopically retracted from one another; and
    maneuvering said actuator so that the two pieces are telescopically moved away from one another to a position with the implant bearing against plates of both the adjacent vertebral bodies.

* * * * *